United States Patent [19]

Shen et al.

[11] Patent Number: 5,834,254
[45] Date of Patent: *Nov. 10, 1998

[54] STABILIZED ENZYME COMPOSITIONS FOR NUCLEIC ACID AMPLIFICATION

[75] Inventors: Nancy Lau Liu Shen; Daniel Louis Kacian; James Garfield Putnam; William Michael Davis, all of San Diego, Calif.

[73] Assignee: Gen-Probe Incorporated, San Diego, Calif.

[*] Notice: The term of this patent shall not extend beyond the expiration date of Pat. Nos. 5,556,771 and 5,614,387.

[21] Appl. No.: 898,570

[22] Filed: Jul. 22, 1997

Related U.S. Application Data

[63] Continuation of Ser. No. 444,528, May 19, 1995, abandoned, which is a continuation of Ser. No. 387,011, Feb. 10, 1995, Pat. No. 5,556,771.

[51] Int. Cl.$^6$ .......................... C12P 19/34; C07H 21/04; C07K 1/00; A23J 1/00
[52] U.S. Cl. .......................... 435/91.2; 435/6; 435/911; 435/193; 435/199; 536/24.3; 536/24.31; 536/24.33; 530/350; 530/412; 530/421; 530/427
[58] Field of Search .............................. 435/6, 91.1, 91.2, 435/193, 199, 810; 536/24.3, 24.31, 24.33; 530/350, 421, 412, 427

[56] References Cited

U.S. PATENT DOCUMENTS

| | | | |
|---|---|---|---|
| 4,451,569 | 5/1984 | Kobayashi et al. | 435/188 |
| 4,806,478 | 2/1989 | Stahl | 435/180 |
| 5,240,843 | 8/1993 | Gibson et al. | 435/188 |
| 5,250,429 | 10/1993 | Jolly et al. | 435/196 |
| 5,556,771 | 9/1996 | Shen et al. | 435/91.2 |
| 5,614,387 | 3/1997 | Shen et al. | 435/91.2 |

FOREIGN PATENT DOCUMENTS

| | | |
|---|---|---|
| 0091258 | 10/1983 | European Pat. Off. . |
| 0270799 | 6/1988 | European Pat. Off. . |
| 0365685 | 5/1990 | European Pat. Off. . |
| 0431882 | 6/1991 | European Pat. Off. . |
| 0448146 | 9/1991 | European Pat. Off. . |
| 8700196 | 1/1987 | WIPO . |
| 8900012 | 1/1989 | WIPO . |
| 8906542 | 7/1989 | WIPO . |
| 9300807 | 1/1993 | WIPO . |
| 9313752 | 7/1993 | WIPO . |
| 9416107 | 7/1994 | WIPO . |

OTHER PUBLICATIONS

Caluso et al. Bio/Technology 10:1007–1011, 1992.
Stratagene Cloning Systems 1992 Product Catalog, pp. 133, 139.
Hilderson et al, "A study on the RNA polymerase activities in bovine thyroid nuclei isolated in isotonic sucrose, hypertonic sucrose or in anhydrous glycerol media", Int. J. Biochem. 16(1):31–37, 1984.
Tersmette et al, "Thermal inactivation of human immunodeficiency virus in lyophilised blood products evaluated by ID50 titrations", Vox Sanguinis 51:239–243, 1986.
Baust, Protective agents: regulation of synthesis. *Cryobiology* 20:357–364 (1983).
Carpenter, et al., Stabilization of phosphofructokinase with sugars during freeze–drying: characterization of enhanced protection in the presence of divalent cations. *Biochimica et Biophysica Acta* 923: 109–115 (1987).
Carpenter, et al., Stabilization of phosofroctokinase during air–drying with sugars and sugar/transition metal mixtures. *Cryobiology* 24: 455–464 (1987).
Carpenter, et al., Long–term preservation of dried phosofroctokinase by sugars and sugar/zinc mixtures. *Cryobiology* 25:372–376 (1988).
Clegg, et al., Cellular responses to extreme water loss: the water replacement hypothesis. *Cryobiology* 19:306–316 (1982).
Crowe, et al., Interactions of sugars with membranes. *Biochimica et Biophysica Acta* 947:367–384 (1988).
Crowe, John H. and Crowe, Lois M., Factors affecting the stability of dry liposomes. *Biochimica et Biophysica Acta* 939:327–334 (1988).
Roser, Bruce, Trehalose drying: a novel replacement for freeze–drying. *BioPharm*, 47–53 (Sep., 1991).

*Primary Examiner*—W. Gary Jones
*Assistant Examiner*—Jeffrey Fredman
*Attorney, Agent, or Firm*—Carlos A. Fisher; Charles B. Cappellari

[57] ABSTRACT

Stabilized enzyme compositions for use in nucleic acid amplification. Compositions are provided for the stabilization of one or more enzymes in a single stabilized formulation. Additional compositions incorporate a dried, stabilized enzyme mixture together with necessary cofactors and enzyme substrates in a single container for use upon rehydration. Also disclosed are methods for making and using stabilized enzyme compositions and kits for nucleic acid amplification incorporating the disclosed compositions.

18 Claims, No Drawings

STABILIZED ENZYME COMPOSITIONS
FOR NUCLEIC ACID AMPLIFICATION

This application is a continuation of application Ser. No. 08/444,528, filed May 19, 1995, now abandoned, which was a continuation of application Ser. No. 08/387,011, filed on Feb. 10, 1995, and issued Sep. 17, 1996, as U.S. Pat. No. 5,556,771.

FIELD OF THE INVENTION

This invention relates to the fields of molecular biology, nucleic acid amplification and stabilized biological compositions generally. In particular, the present invention relates to a stable lyophilized enzyme composition containing one or more nucleic acid polymerases.

BACKGROUND OF THE INVENTION

Deoxyribonucleic acid (DNA) and ribonucleic acid (RNA) are large linear macromolecules composed of covalently-linked nucleotide subunits. DNA is usually found in a "double-stranded" form in which two DNA chains are associated by hydrogen bonding in an antiparallel fashion. RNA usually exists in nature as a single polynucleotide chain. Nucleotides are molecules having a sugar (either deoxyribose or ribose) and a nitrogenous base moiety, and are usually connected together in nucleic acids by a phosphodiester linkage. There are five common nitrogenous bases. Three are found in both DNA and RNA: these are adenine (A), guanine (G) and cytosine (C). The other two, thymine (T) and uracil (U), are specific to DNA and RNA, respectively.

Most (if not all) of every organism's genetic information is transmitted from one generation to the next in the form of DNA or RNA. This information is conveyed in the sequence of the nucleotides along a single nucleic acid chain or "strand", which constitutes a genetic code. Moreover, each of the nitrogenous bases of a nucleic acid strand has the ability to specifically hydrogen bond with one or more other nitrogenous bases of the same or a different nucleic acid strand. Thus, under usual conditions, A hydrogen bonds with T (or U), and C hydrogen bonds with G; this specific hydrogen-bonding is called base-pairing. In double-stranded DNA each of the two strands consists of a chain of nucleotides in which most or all of the nucleotides are base-paired with nucleotides of the other strand. In such a case, the order of nucleotides on one DNA strand determines the order of nucleotides on the other DNA strand. Two nucleic acid strands which are "mirror images" of each other in this way are said to be perfectly complementary.

Nucleic acids are synthesized in vivo by a mechanism exploiting the fact that each nucleic acid strand dictates the order of nucleotides of a perfectly complementary strand; this remains true whether the desired nucleic acid is RNA or DNA, and regardless whether the nucleic acid to be used as a template is RNA or DNA. Most of the specific mechanisms for DNA replication involve the use of a DNA polymerase to sequentially add nucleotides to a 3' hydroxyl group of a polynucleotide primer hydrogen-bonded to the template nucleic acid strand. The newly added nucleotides are chosen by the DNA polymerase based on their ability to base-pair with the corresponding nucleotide of the template strand. This process of adding nucleotides to one end of a primer is sometimes called primer extension.

Unlike DNA synthesis, RNA synthesis does not normally require the existence of a polynucleotide primer. Rather, RNA synthesis is usually mediated by an RNA polymerase which recognizes one or more specific nucleotide sequences of a nucleic acid template. The region of the template to which the RNA polymerase binds, called a promoter, is usually double-stranded. After binding to the promoter, the RNA polymerase "reads" the template strand and synthesizes a covalently-linked polyribonucleotide strand complementary to the template. RNA polymerases from different organisms preferentially recognize different promoter sequences.

DNA and RNA polymerase enzymes have been purified from a number of diverse organisms. Some of these enzymes, such as *E. coli* DNA polymerase I, the Klenow fragment of DNA polymerase I, and various RNA polymerases are commonly used in vitro as tools in molecular biology and nucleic acid biochemistry research. See generally e.g., Sambrook et al., *Molecular Cloning: A Laboratory Manual* (2d ed. Cold Spring Harbor Press 1989).

Another use for nucleic acid polymerases has arisen with the advent of various methods of nucleic acid amplification, such as the polymerase chain reaction (PCR), see e.g., Mullis et al., U.S. Pat. Nos. 4,683,195, 4,683,202, and 4,800,159. In the simplest form of PCR, two oligonucleotide primers are synthesized, each primer complementary to a region of a target nucleic acid positioned to the 3' side, with respect to the target nucleic acid, of a target nucleotide sequence region. Each primer is complementary to one of two complementary nucleic acid strands; the target region comprises a nucleotide sequence region encompassing both nucleic acid strands of a double-stranded target nucleic acid. When these primers are allowed to hydrogen-bond ("hybridize") with the substrate and a DNA polymerase is added to the reaction mixture along with nucleotide triphosphates, each hybridized primer is extended by the enzyme in a 5'→3' direction. The reaction mixture is then heated to melt the primer extension product:template hybrid, the temperature is decreased to permit another round of primer/target hybridization, and more DNA polymerase is added to replace the DNA polymerase inactivated by the high temperature step. By repeating the process through a desired number of cycles, the amount of nucleic acids having the target nucleotide sequence is exponentially increased. More recently, a thermostable DNA polymerase derived from *Thermus aquaticus* has been successfully used in the PCR method to lessen the need for repeated addition of large amounts of expensive enzyme. The Taq polymerase resists inactivation at 90°–95° C., thus obviating the need for repeated additions of enzyme after each round of strand separation.

Other methods of nucleic acid amplification have been devised, such as those using RNA transcription as a step in the amplification process. One such method functions by incorporating a promoter sequence into one of the primers used in the PCR reaction and then, after amplification by the PCR method, using the double-stranded DNA as a template for the transcription of single-stranded RNA by a DNA-directed RNA polymerase, see e.g., Murakawa et al., *DNA* 7:287–295 (1988)).

Other amplification methods use multiple cycles of RNA-directed DNA synthesis and transcription to amplify DNA or RNA targets, see, e.g., Burg et al., WO 89/1050; Gingeras et al., WO 88/10315 (sometimes called transcription amplification system or TAS); Kacian and Fultz, EPO Publication No. EPO 408,295 (which enjoys common ownership with the present application); Davey and Malek, EPO Application No. 88113948.9; Malek et al., WO91/02818). These methods make use of an enzyme, reverse transcriptase (RT), which can use RNA or DNA as a template for synthesis of a complementary DNA strand. Some of these methods also utilize cellular RNAse H activity as an essential component. Most retroviral reverse transcriptases, such as those encoded by Moloney Murine Leukemia virus (MMLV) and Avian Myeloblastosis Virus (AMV), possess an RNA-directed DNA polymerase, a DNA-directed DNA polymerase activity as well as RNaseH activity. RNAse H activity selectively degrades the RNA strand of an RNA:DNA hybrid nucleic acid molecule, thus allowing the amplification reaction to proceed without the need for temperature cycling.

Nucleic acid amplification is an increasingly popular tool for the specific identification and/or amplification of unique or characteristic nucleic acid segments in a variety of settings. Thus, nucleic acid amplification is used in food and agricultural testing, medical diagnostics, human genetic testing and counseling, archeology, and criminal forensics. Because these methods all utilize enzymes, methods of producing, packaging, transporting and storing large quantities of highly active enzymes has become an issue of critical importance in the manufacture, marketing and sale of enzymes and kits for nucleic acid amplification. Specifically, for methods employing transcription-based amplification, commercially acceptable methods and preparations for storing active preparations of reverse transcriptase and RNA polymerase are necessary for the successful manufacture and marketing of kits for nucleic acid amplification.

The usual method of stabilizing reverse transcriptase and RNA polymerase enzymes (as well as many other enzymes used in molecular biology research) is by storing a liquid preparation of each enzyme in a solution containing 50% (v/v) glycerol and a reducing agent such as dithiothreitol (DTT) or β-mercaptoethanol (βME) at −20° C. This method preserves the activity of the enzymes for many months with little loss of activity. By contrast, enzyme activities are readily lost when the enzymes are stored at room temperature or at 4° C. These preparations are generally shipped from the enzyme supplier to the end user in dry ice; losses of 30% or more of enzyme activity are common during such transport due to freezing and thawing of the enzyme preparation. These enzymes are formulated and supplied separately.

A method of storing and shipping reverse transcriptase and RNA polymerase without the need for refrigeration would obviate the necessity for refrigerated transport and/or methods of cold storage such as dry ice, wet packs, dry packs, or styrofoam shipping containers. Such methods would also be more cost effective, since the production overhead associated with these methods of maintaining enzyme activity would be unnecessary. Methods of storing enzymes which would allow the enzyme preparation to tolerate a limited exposure to higher temperatures would eliminate the losses in enzyme activity which could result if the enzyme preparation sits on a loading dock or in a truck during shipment. Such a method would have to be highly reproducible. Moreover, if the enzymes could be provided in a single container in a form compatible with their intended use (such as in a formulation containing all or most of any necessary co-factors and substrates) such a preparation would be more economical to manufacture and more convenient to use.

Freeze-drying (lyophilization) has been used to preserve foods, biological membranes, whole cells (see, e.g., American Society for Microbiology, *Manual of Methods for General Bacteriology* 210–217 (1981), and biological macromolecules including enzymes. Lyophilization involves the removal of water from a frozen sample by sublimation under lowered pressure. Sublimation is the process by which a solid is evaporated without passing through the liquid stage.

The theoretical aspects of lyophilization are complex. It is thought that when a biological substance such as a protein is in aqueous solution the molecule is surrounded by a hydration shell comprising water molecules; this hydration shell stabilizes the protein and helps maintain its activity. When water is removed, the protein's reactive groups, which are normally masked by the hydration shell, are free to react with each other, thus forming new, essentially irreversible bonds. These bonds can distort the protein's native conformation. Also, new hydrophobic/hydrophilic interactions may take place in the absence of water which also can distort the conformation of the protein. Since the three-dimensional conformation of many proteins confers a biological activity, the distortion of the conformation can alter biological activities upon drying. By the same mechanism, cross-linking and aggregation of proteins can occur.

Freezing a protein sample prior to drying helps reduce the degree of conformational distortion due to drying. The lowered initial temperature helps keep unwanted reactions between amino acid reactive groups to a minimum by depriving the reactants of energy. At the same time, while in a frozen state the protein has less stearic freedom than when in solution and is less prone to gross conformational change.

However, completely dried lyophilizates tend to have a shorter "shelf" or storage life than do incompletely dried lyophilizates still containing a low percentage of water.

Such incompletely dried lyophilizates must often be stored at temperatures no higher than about 4°–10° C., and are still capable of undergoing inactivating chemical reactions that would not be possible were water not present. Thus, while the shelf life of many incompletely dried lyophilized biologically active proteins is longer than those that are completely dried, it is still necessary to refrigerate the preparation in order to maintain activity. Even so, there is a loss of activity in such preparations over a relatively short period of time. Moreover, some enzymes, such as phosphofructokinase, are completely inactivated after lyophilization in the absence of a cryoprotectant, regardless of whether the preparation is completely dried or not. See e.g., Carpenter et al., *Cryobiology* 25:372–376 (1988).

As used herein, the term "cryoprotectant" is intended to mean a compound or composition which tends to protect the activity of a biologically active substance during freezing, drying, and/or reconstitution of the dried substance.

The term "stabilizing agent" is meant to mean an agent that, when added to a biologically active material, will prevent or delay the loss of the material's biological activity over time as compared to when the material is stored in the absence of the stabilizing agent.

A variety of cryoprotectant additives have been used or proposed for use as excipients to help preserve biological activity when biological materials, including particular proteins, are dried. Clegg et al., *Cryobiology* 19:106–316 (1982) have studied the role of glycerol and/or trehalose in the ability of cysts of the brine shrimp Artemia to remain viable after desiccation. Carpenter et al., *Cryobiology* 24: 455–464 (1987), report that the disaccharides maltose, sucrose, lactose and trehalose can play a role in increasing the stabilization of phosphofructokinase activity in a purified enzyme preparation subjected to air-drying. EPO Publication No. 0431882A2, discloses a stabilized preparation of purified alkaline phosphatase that had been derivatized and then lyophilized in the presence of mannitol or lactose. EPO Publication No. 0091258A2, discloses a method for stabilizing tumor necrosis factor (TNF) by storage or lyophilization of the purified protein in the presence of a stabilizing protein, such as human serum albumin, gelatin, human γ globulin, or salmon protamine sulfate. U.S. Pat. No. 4,451, 569 discloses the use of pentoses, sugar alcohols and some disaccharides to stabilize the activity of purified glutathione peroxidase. The stabilized composition may be freeze-dried and then stored at temperatures below 20° C. EPO Publication No. 0448146A1 discusses stabilized, lyophilized gonadotropin preparations containing a dicarboxylic acid salt. The preparation can further contain a disaccharide such as sucrose or trehalose. Roser, *Biopharm*, 47–53 (September 1991) discusses preserving the biological activity of various biological molecules dried at ambient temperature using trehalose. PCT Publication No. WO87/00196 reports the stabilization of monoclonal antibodies and calf intestine alkaline phosphatase by air drying in the presence of trehalose. PCT Publications WO89/00012 and WO89/06542 discuss the use of trehalose to preserve some foods and the antigenicity of live virus particles. EPO Publication 02270799A1 reports the stabilization of recombinant β-interferon in a formulation containing a stabilizing agent such as a detergent or glycerol. The compositions can further comprise various sugars including sucrose and trehalose, sugar alcohols, and proteins as additional stabilizing agents; most preferred among these is dextrose.

Some of these additives have been found to extend the shelf life of a biologically active material to many months or more when stored at ambient temperature in an essentially dehydrated form. However, the effectiveness, suitability or superiority of a particular prospective additive depends on the chemical composition of the biologically active material sought to be stabilized; in the case of a protein these factors may include, without limitation, the amino acid sequence of the protein, and its secondary, tertiary and quaternary structure. Thus, whether a particular composition will function to preserve biological activity for a particular biologically active material is not a priori predictable.

Moreover, if a protein is lyophilized, additional factors including, without limitation: the buffer composition, the speed of freezing, the amount of negative pressure, the initial, operating and final lyophilization temperatures and the length of the lyophilization procedure are important in determining the stability and shelf life of the active protein.

Some proteins are known to have multiple enzymatic activities. Thus, retroviral reverse transcriptase enzymes such as those derived from Moloney Murine Leukemia Virus (MMLV-RT) have a DNA-directed DNA polymerase activity, an RNA-directed DNA polymerase activity, and an RNAse H activity. While these activities are contained in the same enzyme, conditions for the preservation of any one of these activities in a dried preparation does not assure that one or both of the remaining enzyme activities will also be preserved under the same conditions.

Moreover, when a particular application requires that the balance of relative specific activities of the three activities of reverse transcriptase remain similar after reconstitution to the balance of these activities before drying, as in the transcription-based nucleic acid amplification system of Kacian & Fultz, supra (which enjoys common ownership with the present application and is incorporated by reference herein), a particular preservation method may upset the delicate balance of these enzymatic activities, thereby making the enzyme unsuitable for such use. Thus, if the RNaseH activity of the enzyme is preserved more than the RNA-directed DNA polymerase activity, the RNA:DNA initiation complex may be degraded before DNA synthesis can begin.

Since a given cryoprotectant composition effective for the long-term preservation of a given enzymatic activity is not clearly effective or superior when applied to another enzymatic activity, different enzymes often require quite different protestants for activity stabilization. As a result, among commercially manufactured lyophilized enzyme preparations, all or most contain only a single enzyme dried in a formulation customized to preserve the activity of that specific enzyme.

SUMMARY OF THE INVENTION

The present invention is directed to compositions and kits comprising dried formulations of reverse transcriptase and RNA polymerase able to be stored at ambient temperature for prolonged periods of time without substantial losses of enzymatic activities. Preferably, the formulations comprise preparations of retroviral reverse transcriptase and/or bacteriophage RNA polymerase. More preferably, the formulations comprise reverse transcriptase derived from Moloney Murine Leukemia Virus (MMLV-RT) and bacteriophage T7 RNA polymerase in a cryoprotectant excipient. Even more preferably, the invention is directed to single containers comprising dried formulations containing both MMLV-RT and T7 RNA polymerase in one or more cryoprotectant excipients. Most preferably, the invention is directed to single containers comprising dried formulations containing MMLV-RT and T7 RNA polymerase, one or more cryoprotectant excipients comprising either or both trehalose and polyvinylpyrrolidone (PVP), nucleotide triphosphates, and metal ions and co-factors necessary for said enzymatic activities wherein, upon reconstitution of the stabilized lyophilizate and addition of a target nucleic acid and one or more appropriate primers, the formulation is in a convenient and cost-effective form for nucleic acid amplification without the need for excessive handling. Optionally, such a formulation may contain primers for initiation of nucleic acid synthesis. Lastly, the present invention is directed to methods of making and using the dried formulations described above.

Reverse transcriptase and RNA polymerase enzymes are important agents in transcription-mediated nucleic acid amplification methods, such as those described in Burg et al., supra; Gingeras et al., supra, (sometimes called transcription amplification system or TAS); Kacian and Fultz, supra; Davey and Malek, EPO Application No. 8811394-8.9 and Malek et al., PCT Publication No. WO91/02818). Such methods are increasingly important in fields such as forensics and medical diagnostics, where the stability of the amplification reagents over time is an significant consideration in the cost of manufacturing, marketing and use of products which employ nucleic acid amplification.

Applicant has discovered a method and a dried formulation for the preservation of the DNA-directed DNA polymerase, RNA-directed DNA polymerase, and RNAse H activities of reverse transcriptase. The same method and formulation has been discovered to be suitable for the preservation of RNA polymerase activity. Moreover, Applicant has surprisingly found that both enzymes and all four enzymatic activities can be stabilized and preserved as a dried formulation in a single container without significant loss of any of the four activities over a substantial period of time, even after prolonged incubation at high temperature.

One aspect of the present method comprises providing an active purified reverse transcriptase with a cryoprotectant excipient comprising a non-reducing disaccharide (preferably sucrose or trehalose), or polyvinylpyrrolidone (PVP), or an amount of a mixture of these compounds effective to act as an agent protecting and preserving the DNA-directed DNA polymerase, RNA-directed DNA polymerase, and RNAse H activities of reverse transcriptase after drying the enzyme by methods such as, without limitation, lyophilization of a solution containing reverse transcriptase and the cryoprotectant.

In a second aspect, the invention features a method for stabilizing and preserving active purified RNA polymerase, preferably T7 RNA polymerase, in a dehydrated form substantially stable at room temperature for more than 90 days. In this aspect, the RNA polymerase is dried in the presence of metal salts, such as those containing $Mg^{++}$ or $Zn^{++}$, one or more protective stabilizing agents selected from the group consisting of non-reducing disaccharides, preferably trehalose, and polyvinylpyrrolidone (PVP), and a reducing agent, such as n-acetyl-L-cysteine (NALC). While not wishing to be limited by theory, Applicant believes that the reducing agent helps to prevent inactivation of the enzyme through oxidation of any cysteine residues present in the enzyme. In this aspect, the RNA polymerase retains at least 70% of its original activity, preferably after exposure of the dehydrated formulation to a temperature of 45° C. for at least 30 days or 35° C. for at least 61 days.

In another aspect, the invention features a single dried formulation containing a mixture of reverse transcriptase (preferably MMLV-RT), RNA polymerase (preferably T7 RNA polymerase), an amount of a cryoprotectant excipient (preferably trehalose and/or polyvinylpyrrolidone) effective to preserve the enzymatic activities of the dried enzymes, nucleotide triphosphates, necessary co-factors, optional oligonucleotide primers, and a reducing agent, preferably a thiol compound.

In yet another aspect, the present invention comprises a component of a kit for the amplification and specific identification of nucleic acids belonging to one or more phylogenetic groupings of organisms, for example for the specific detection of one or more species within a genus or one or more genera within a family. The invention provides a reconstitutable dried formulation comprising a reverse transcriptase, an RNA polymerase, ribonucleotide triphosphates, deoxyribonucleotide triphosphates, zinc and/or magnesium salts, and a reducing agent in a single container. Amplification primers and an aqueous reconstitution solution may be supplied as one or more additional separate components of the kit. Alternatively, amplification primers may be comprised in the dried formulation. Target sequence-specific nucleic acid hybridization assay probes and any desired unlabeled helper oligonucleotides may be included in the dried formulation or provided in a separate reagent. Upon reconstitution of the dried formulation and addition of the oligonucleotide primers (if not already present), the mixture is contacted with a partially or wholly single-stranded target nucleic acid. If the target nucleic acid has nucleotide sequences complementary to the primer(s) (or the primer portion of a promoter-primer(s)), the reaction will proceed upon incubation of the reaction mixture at a temperature sufficient for nucleic acid amplification.

In another aspect, the invention comprises a single lyophilizate containing a combination of reverse transcriptase (preferably MMLV-RT), RNA polymerase (preferably T7 RNA polymerase), a cryoprotectant excipient, nucleotide triphosphates, necessary co-factors and a reducing agent, preferably containing a thiol group. The lyophilizate may be transported and stored without the need for refrigeration, and can withstand transient exposure to elevated temperatures, for example, without limitation, 55° C. for 30 days, without significant diminution of enzyme activity.

By "nucleotide triphosphates" is meant ribo- or deoxyribonucleotide triphosphates and derivatives thereof which are able to serve as substrates for an RNA polymerase and a DNA polymerase, preferably a reverse transcriptase, respectively. Such derivatives may include, without limitation, nucleotides having methyl (or other alkyl) and/or sulfur groups incorporated at the nitrogenous base (usually adenine, thymine or uracil, cytosine and guanine), the ribose or deoxyribose moiety, or the phosphate group.

By "nucleotide" is meant a nucleic acid subunit comprising a single nitrogenous base (usually adenine, thymine or uracil, cytosine and guanine), a sugar moiety (ribose or deoxyribose) and a phosphate group. As used herein, the term refers both to unincorporated ribo- or deoxyribonucleotide triphosphates and to the covalently-linked nucleotide subunits of an oligonucleotide or nucleic acid strand, depending upon the context of usage.

DETAILED DESCRIPTION OF THE INVENTION

The present invention involves methods for stabilizing the enzymatic activities of DNA polymerase and RNA polymerase enzymes by removing the solvent from a solution containing one or more of these enzymes in the presence or a cryoprotectant, or stabilizing "bulking agent". Such cryoprotectants include saccharides, particularly non-reducing disaccharides, and water soluble polymers having electropositive and/or electronegative groups available for hydrogen-bonding with the enzyme. Particularly preferred cryoprotectants are the disaccharides sucrose and trehalose and the polymer polyvinylpyrrolidone (PVP).

The present invention also relates to stabilized compositions comprising a desiccated DNA polymerase, a desiccated RNA polymerase, or a desiccated mixture containing both a DNA polymerase and an RNA polymerase. Preferred enzymes comprising these compositions are reverse transcriptases and bacteriophage RNA polymerases; particularly preferred enzymes are the retroviral reverse transcriptase from Moloney Murine Leukemia Virus and the RNA polymerase from bacteriophage T7.

A preferred method of desiccating the DNA polymerase and RNA polymerase of the present invention is by lyophilization. In this process, a solution containing the enzyme is frozen, a vacuum applied to the frozen enzyme solution, and the solvent removed from the preparation by sublimation, leaving behind the solutes.

The present invention also features a composition for the replication of one or more particular nucleic acid sequences which includes a desiccated preparation of a DNA polymerase (preferably a reverse transcriptase), an RNA polymerase, nucleotide triphosphates, and co-factors necessary for enzyme activity. The desiccated preparation may also contain amplification primers for the specific replication of the target nucleotide sequence and/or hybridization assay probes and helpers. Preferably, the desiccated composition is prepared by lyophilization.

The compositions of the present invention are stable for a prolonged period, even when stored at high temperatures. Such compositions are thus useful in shipping and storage of commercial preparations of these enzymes and of kits for nucleic acid amplification which contain these enzymes.

EXAMPLES

It will be understood that the following examples are intended to illustrate various presently preferred embodiments of the present invention and do not in any way limit its scope. Nor is the disclosure of an embodiment a representation that other embodiments of the invention might not exist which are more effective to achieve one or more object sought to be addressed by the present invention.

Example 1

Lyophilization of Reverse Transcriptase and RNA Polymerase

The reverse transcriptase used in this and the following examples was either a recombinant Moloney Murine Leukemia Virus reverse transcriptase expressed in *E. coli* strain 1200 and purified from a cell paste or a commercially available, purified MMLV-RT preparation obtained from United States Biochemicals, Cleveland, Ohio.

The enzyme preparation was stored at −20° C. in a storage buffer containing 20–50 mM Tris-HCl (pH 7.5), 0.1M NaCl, 0.1 mM ethylenediamine tetraacetic acid (EDTA), 1.0 mM dithiothreitol (DTT), 0.01% (v/v) TERGITOL NP®-40 (TERGITOL NP® is a registered trademark of Union Carbide Chemicals and Plastics Co., Inc.) or 0.1% (v/v) TRITON® X-100 (TRITON® is a registered trademark of Union Carbide Chemicals and Plastics Co., Inc.), and 50% (v/v) glycerol. Purified T7 RNA polymerase was obtained from Epicentre Technologies, Madison, Wis. Prior to dialysis the enzyme was stored in 50% (v/v) glycerol, 50 mM Tris-HCl (pH 7.5), 0.1M NaCl, 1.0 mM DTT, 0.1 mM EDTA and 0.1% (v/v) TRITON® X-100. This enzyme was also stored at −20° C. prior to dialysis.

Three enzyme preparations were dialyzed in preparation for lyophilization. The first preparation contained 324,012 units of MMLV-RT diluted into a buffer containing 20 mM HEPES ([2-hydroxyethyl] piperazine-N'-[2-ethanesulfonic acid]) (pH 7.5), 0.1M NaCl, 0.1 mM EDTA, 2 mM NALC, 0.1 mM zinc sulfate, 0.2M trehalose and water. The final volume was 720 μl. This was dialyzed against 250 ml of the same buffer (Trehalose Buffer) for 6 hours at 4° C. The dialysis membranes were prepared by boiling in 2% (w/v) sodium bicarbonate and 10 mM EDTA (pH 8.0), then in 10 mM EDTA (pH 8.0), and finally in deionized water for 10 minutes each time. The membranes were then thoroughly rinsed with deionized water prior to use. The dialysis buffer was changed with the same volume of fresh buffer and dialysis continued for an additional 10 hours. Buffer was changed again and continued for another 3 hours. The final volume was 655 μl.

The second preparation contained 144,000 units of T7 RNA polymerase in 720 μl. This was dialyzed against Trehalose Buffer on the same schedule and in the same volumes as the reverse transcriptase preparation. Final volume was 1270 μl.

The third preparation contained both reverse transcriptase and RNA polymerase; 324,012 units of reverse transcriptase and 144,000 units of RNA polymerase were combined to a final volume of 1440 μl. This was dialyzed against 3 equal volumes of Trehalose Buffer on the same schedule as the other two preparations. The final volume of the dialysate was 1975 μl.

After dialysis, each preparation was divided into 12 equal aliquots in vials. Each vial contained 27,000 units of reverse transcriptase, 12,000 units of T7 RNA polymerase, or both enzymes in these amounts. The vials were placed in a programmable Virtis model lyophilizer 101-SRC with a FCP-III control system. The vials were cooled to −40° C. in approximately 5 minutes. Lyophilization was commenced by decreasing the pressure to −180 Torr; the vacuum was kept constant throughout the lyophilization protocol. The temperature was then raised in a linear fashion to −10° C. during the following 2 hours and maintained at this temperature for the next 6 hours. The temperature was then linearly raised to 10° C. over the next hour, and maintained at 10° C. for 4 hours. The temperature was again linearly ramped up to 25° C. over the next 30 minutes and maintained at 25° C. for the following 10.5 hours. The pressure was then returned to atmospheric with the introduction of dry nitrogen, and the vials were sealed under nitrogen before their removal from the lyophilizer. The vials were then stored at 25° C. for 22 days.

After the storage period, the lyophilized enzyme preparations were reconstituted in Reconstitution Buffer (0.01% (v/v) TRITON® X-100, 41.6 mM $MgCl_2$, 1 mM $ZnC_2H_3O_2$, 10% (v/v) glycerol, 0.3% (v/v) ethanol, 0.02% (w/v) methyl paraben, and 0.01% (w/v) propyl paraben) and assayed for their ability to support nucleic acid amplification.

Reaction mixtures of 90 μl total volume were prepared containing 50 mM Tris-HCl (pH 8.0), 17.5 mM, 2 mM spermidine, 25 mM KCl, 2 mM each of dATP, dCTP, dTTP and dGTP, 2.5 mM CTP and UTP, 6.5 mM ATP and GTP, 5 mM DTT, 0.44 μl of a 675 μg per ml solution of a promoter-primer (SEQ ID NO: 1) having a target binding region complementary to a region of one strand of bacteriophage T7 Gene 10, 0.3 μl of a 451 μg per ml solution of a primer (SEQ ID NO: 2) having a target binding region complementary to the other strand of bacteriophage T7 Gene 10, one hundred copies of the T7 Gene 10 target nucleic acid and water. The T7 Gene 10 RNA target was a (+) sense transcript of a plasmid-borne T7 Gene 10 restriction fragment derived from plasmid pGEMEX-1 (Promega Corporation, Madison, Wis.). The purified RNA transcript was present at a concentration of 0.61 picomoles/μl. One hundred copies of the target nucleic acid were added to each tube. Each tube was also overlayed with 200 μl of mineral oil to prevent evaporation of the sample during the assay.

All tubes were incubated at 95° C. for 5 minutes and allowed to cool to room temperature before the addition of enzyme reconstituted as described above; while this step is not necessary when the target nucleic acid is RNA or single-stranded DNA rather than double-stranded DNA, an initial heat step helps to melt any regions of RNA intramolecular hydrogen-bonding. The experimental tubes containing the separately lyophilized enzyme preparations were then given 10 μl of a solution containing 400 units of T7 RNA polymerase and either 600 or 900 units of lyophilized MMLV-RT; the co-lyophilized T7 RNA polymerase and MMLV-RT were present at concentrations of 400 units and 900 units per 10 μl, respectively. The tubes were incubated at 37° C. for 3 hours.

The amount of amplified nucleic acid produced during the reaction was determined using the homogeneous protection assay described in Arnold and Nelson, U.S. Pat. No. 5,283,174 (which enjoys common ownership with the present application and which is incorporated by reference herein); it will be clear to one of skill in the art that many other assay systems and methods of detecting a nucleic acid target, such as by employing radiolabeled probes, are available in the art.

The amplification reaction was terminated with the addition to each tube of 100 μl of a hybridization buffer containing 200 mM lithium succinate (pH 5.2), 17% (w/v) lithium lauryl sulfate, 3 mM EDTA (ethylenediamine tetraacetic acid) and 3 mM EGTA ([ethylenebis (oxyethylenitrilo)]-tetraacetic acid)) and an acridinium ester-labeled probe (SEQ ID NO: 3) complementary to the T7 Gene 10 RNA transcript. The tubes were incubated at 60° C. for 20 minutes. The acridinium ester associated with unhybridized probe was hydrolyzed with the addition of 300 μl of 182 mM NaOH, 600 mM boric acid and 1% (v/v) TRITON® X-100 and the tubes incubated at 60° C. for 5 minutes. The remaining chemiluminescence was measured in a luminometer upon the addition of 200 μl of 1% (v/v) $H_2O_2$ in 0.4N $HNO_3$ followed immediately with alkalination of the solution with the immediate addition of (200 ul) 1M NaOH. The results are reported in relative light units (RLU), which is a measure of the number of photons emitted by the chemiluminescent label. Results are shown in Table 1 below.

TABLE 1

Comparison of Lyophilized Enzymes Stored at 25° C. for 22 days with Unlyophilized Enzymes

|  | RNA Target | | Negative Control | |
| --- | --- | --- | --- | --- |
|  | 600 units MMLV-RT and 400 units of T7 polymerase | 900 Units MMLV-RT and 400 units of T7 polymerase | 600 units MMLV-RT and 400 units of T7 polymerase | 900 Units MMLV-RT and 400 units of T7 polymerase |
| Liquid MMLV-RT and Liquid T7 RNA polymerase | 321329 | 428872 | 1868 | 5630 |
| Lyophilized MMLV-RT and Liquid T7 RNA polymerase | 301253 | 463561 | 1681 | 1684 |
| Liquid MMLV-RT and Lyophilized T7 RNA polymerase | 549204 | 343582 | 1366 | 1545 |
| Lyophilized MMLV-RT and Lyophilized T7 RNA polymerase (Separately Lyophilized) | 415080 | 493779 | 1352 | 1374 |
| Co-Lyophilized MMLV-RT and T7 RNA polymerase | 677531 (900 units MMLV-RT) | 654359 | 1376 (900 units MMLV-RT) | 1296 |

These results indicate that the co-lyophilized MMLV-RT and T7 RNA polymerase caused amplification of the RNA Gene 10 target more effectively than in reaction mixtures with either enzyme preparation paired with a liquid enzyme preparation of the other enzyme, or where both enzymes were unlyophilized. The was no significant diminution in the ability of any of the lyophilized enzyme preparations to catalyze amplification as compared to the liquid enzymes. Thus, the results also demonstrate that each enzyme can be effectively stabilized by storage in a dried state in the presence of trehalose, either alone or together. Because nucleic acid amplification under these conditions depends on the presence of all three of the enzymatic activities of reverse transcriptase (RNA-directed DNA polymerase, DNA-directed DNA polymerase and RNAse H), the assay is an effective indication both that these activities are effectively stabilized by the present method and that the activities remain coordinated in such a way as to promote nucleic acid amplification.

Additional experiments showed that reverse transcriptase can be lyophilized in the presence of sucrose rather than trehalose under similar conditions; trehalose appeared to be slightly superior to sucrose as a cryoprotectant stabilizing agent. (See Example 6.)

b. Lyophilization of Reverse Transcriptase and T7 RNA Polymerase in the presence of Non-Ionic Detergent Reverse transcriptase and RNA polymerase were co-dialyzed and lyophilized in the presence of a non-ionic detergent in order to attempt to minimize precipitation of protein during the lyophilization procedure while maintaining the enzymatic activity dialysis of the enzymes. Six dialysis mixtures were prepared containing 0%, 0.01%, 0.05%, 0.1%, 0.2%, and 0.5% TRITON® X-102 in a dialysis buffer. The dialysis buffer contained 20 mM HEPES, 0.1M NaCl, 0.1 mM EDTA, 5 mM NALC, 0.1 mM zinc acetate and 0.2M trehalose. Final volume of each dialysis mixture was 250 ml. Four hundred sixty seven microliters of each buffer was combined with 46 μl MMLV-RT (2900 units/μl) and 74 μl T7 RNA polymerase (800 units/μl) for a starting volume for each dialysate of 587 μl. The samples were dialyzed against 60 ml of the corresponding buffer at 4° C. with three changes of the same volume of buffer. Following the third buffer change, a precipitate was seen in the samples containing 0%, 0.01%, and 0.05% TRITON® X-102; no such precipitate was seen in the samples containing 0.1%, 0.2% or 0.5% TRITON® X-102.

After dialysis, the volume of each dialysate was measured and the calculated enzyme concentrations adjusted accordingly. Each sample was divided into 4 vials, with each vial containing 24,750 units of MMLV-RT and 11,000 units of T7 RNA polymerase. Lyophilization was performed as above. The appearance of the detergent-containing lyophilizates after drying was indistinguishable from lyophilizates prepared in the absence of TRITON® X-102. Following lyophilization, the vials were stored at 4° C. and 55° C. for 32 days.

The effect of the non-ionic detergent on the activity of the enzymes was assessed in an amplification assay using the T7 Gene 10 amplification system. Each lyophilized enzyme preparation was rehydrated in Reconstitution Buffer; 900 units of MMLV-RT and 400 units of T7 RNA polymerase were assayed in each reaction mixture. RNA Gene 10 transcripts (100 copies per reaction) were used as the target nucleic acid. The assay was conducted as described above unless expressly indicated otherwise. Results are reported in RLU.

TABLE 2

Stability of Lyophilized Enzymes Upon 32 Days' Storage in the Presence of Detergent

| Sample* | Stored at 4° C. | | Stored at 55° C. | | |
|---|---|---|---|---|---|
| | RNA target (Duplicates) | No Target | RNA Target (Duplicates) | | No Target |
| A | 1612901   1317601 | 1543 | | | |
| B | 1151828   1146113 | 1700 | 791757 | 320417 | 1701 |
| C | 1286845   1219888 | 1544 | 1190527 | 905066 | 1690 |
| D | 1215264   1205790 | 1513 | 1251635 | 1388493 | 1513 |
| E | 1208586   1418260 | 1545 | 1245880 | 1052251 | 1591 |

*Sample A = Unlyophilized enzymes stored at −20° C..
Sample B = Lyophilized enzymes in 0% TRITON ® X-102.
Sample C = Lyophilized enzymes in 0.1% TRITON ® X-102.
Sample D = Lyophilized enzymes in 0.2% TRITON ® X-102.
Sample E = Lyophilized enzymes in 0.5% TRITON ® X-102.

These results demonstrate that a non-ionic detergent such as TRITON® X-102 can effectively prevent the formation of a protein precipitate after dialysis of MMLV-RT or T7 RNA polymerase. The results also show that TRITON® X-102 does not have a deleterious effect upon amplification of the target nucleic acid, and may even act to better stabilize the enzyme activities when the lyophilized enzymes are stored at elevated temperatures over time. The detergent does not cause an increase in the background luminescence in this assay. These results also demonstrate that even the sample lyophilized in the absence of detergent (Sample B) remains approximately as active as non-lyophilized enzymes. The results indicate further that when the lyophilized enzyme preparation is stored at elevated temperature for a prolonged period of time the lyophilized enzyme preparation does not experience detectable diminution in activity.

It will be clear to one of skill in the art that these results immediately suggest that other non-ionic detergents such as, without limitation, detergents of the BRIJ series, the TWEEN series, other detergents of the TRITON series, and the TERGITOL series may be easily screened as indicated above for their ability to maintain the dried proteins in a soluble state during lyophilization without having an adverse effect on enzyme activity.

Example 2
Co-Lyophilization of Reverse Transcriptase and RNA Polymerase with Amplification Reagents Moloney Murine Leukemia Virus reverse transcriptase and T7 RNA polymerase enzyme preparations were kept at −20° C. in a storage buffer containing 50 mM Tris-HCl (pH 7.5), 0.1M NaCl, 0.1 mM EDTA, 1 mM DTT, 0.01% (v/v) NP®-40 or 0.1% (v/v) TRITON® X-100 and 50% (v/v) glycerol prior to drying.

In preparation for lyophilization, $3 \times 10^6$ units of MMLV RT and $1.3 \times 10^6$ units of T7 polymerase (2.5 ml of each preparation) were combined and dialyzed against at least 50 volumes of a buffer containing 20 mM HEPES(pH 7.5), 5 mM NALC, 0.1 mM EDTA, 0.1 mM zinc acetate, 0.2% (v/v) TRITON® X-102, and 0.2M trehalose using dialysis membranes with a molecular weight cutoff of 12,000 Daltons at 2°–8° C. with three changes of the same volume of buffer for at least 8 hours between each buffer change.

Twenty milliliters of the dialyzed enzyme preparation was combined with 60 ml of an Amplification Reagent containing 10.0 mM spermidine, 250 mM imidazole/150 mM glutamic acid (pH 6.8), 99 mM NALC, 12.5% (w/v) PVP, 12.5 mM each of rCTP and rUTP, 31.2 mM each of rATP and rGTP, and 10.0 mM each of dCTP, dGTP, dATP and dTTP (6:2 volume ratio). Additional experiments have shown that the reagents may be combined in a 7:1 volume ratio (Amplification Reagent to enzyme preparation) without significantly different results. Theoretically, the dialyzed enzyme preparation and the Amplification Reagent may be combined in equal proportions; determination of an appropriate ratio of Amplification Reagent to enzyme is well within the ability of the skilled artisan.

The final composition of the combined enzyme:Amplification Reagent preparation prior to lyophilization was: $2.7 \times 10^6$ units of MMLVRT and $1.2 \times 10^6$ of T7 polymerase $6 \times 10^6$ units of each enzyme, 5.0 mM HEPES (pH 6.8 to 7.0), 0.025 mM EDTA, 0.025 mM zinc acetate, 10.0 mM spermidine, 187.5 mM imidazole, 112.5 mM glutamic acid, 75.6 mM NALC, 0.05% (v/v) TRITON® X-102, 9.4% (w/v) PVP (average MW 40,000 Daltons), 0.05M trehalose, 9.4 mM each of rCTP and rUTP, 23.4 mM each of rATP and rGTP, and 7.5 mM each of dCTP, dGTP, dATP and dTTP.

Eight hundred microliters of the combined enzyme:Amplification Reagent preparation (hereafter Enzyme:Amplification Reagent) were placed into each individual glass vial for lyophilization (approximately 39,000 units of total enzymes per vial). Lyophilization was conducted as follows in Example 1. After lyophilization, the vials were then treated as indicated in the following examples.

Example 3
Amplification Activity Assay of Lyophilized Reagent

Freshly lyophilized preparations of reverse transcriptase, RNA polymerase, and Amplification Reagent were incubated at 25° C., 35° C. and 45° C. for various times, ranging from 3 to 61 days. All vials were prepared identically from the same preparation. At the indicated time points vials containing the lyophilized reagents were removed from elevated temperature and stored at −30° C. until the last samples had been collected. Samples representing the "zero" time for each temperature were stored at −30° C. for the entire experimental time period.

When the vials from the last time point had been collected all samples were rehydrated in 1.5 ml of Reconstituting Reagent (0.01% (v/v) TRITON® X-102, 41.6 mm $MgCl_2$, 1 mM $ZnC_2H_3O_2$, 10% (v/v) glycerol, 0.3% (v/v) ethanol, 0.02% (w/v) methyl paraben, and 0.01% (w/v) propyl paraben) and the contents of each vial assayed for the ability to cause nucleic acid amplification.

Activity in a model amplification system was measured in the following way in this example. Each amplification reaction mixture contained 500 copies of a double-stranded DNA restriction fragment from a plasmid containing part of the hepatitis B virus genome as the target nucleic acid (a PUC plasmid containing a 2.6 kb fragment of the hepatitis B virus genome). The target DNA was diluted in 20 μl of either water or human serum. Negative controls were made in the same way, but without target DNA. This was added to 20 μl of a 2× primer solution; the final composition of this solution was 0.1N KOH, 17.5 mM EGTA, 25 mM imidazole, 25 mM glutamic acid, 0.025% (w/v) phenol red, and 0.3 μM of each of two primers in a total volume of 40 μl. The first primer ((−) sense) consisted of a 3' target-binding nucleotide sequence region complementary to the (+) sense strand of the DNA target and a 5' non-complementary region was situated downstream from a 5' non-complementary region having the nucleotide sequence of the promoter for T7 RNA polymerase. The second primer ((+) sense) had a nucleotide sequence consisting of a target-binding region complementary to the other ((−) sense) DNA strand.

Each 40 μl reaction mixture was incubated at about 95° C. to denature the double-stranded DNA target. The reaction was then cooled to room temperature for 5 minutes and neutralized with 10 μl of a buffer containing 330 mM imidazole and 200 mM glutamic acid. Had the target nucleic acid been RNA rather than DNA this denaturation step would not be necessary.

Fifty microliters of each reconstituted Enzyme: Amplification Reagent was given to 50 μl of the denatured, neutralized DNA reaction mixture, which was then incubated at 37° C. for 3 hours. Each reaction was terminated by the addition of 20 μl (40 units) of RNAse-free DNAse I.

The relative amplification of each reconstituted Enzyme:Amplification Reagent was determined by using the homogeneous protection assay (HPA) described in Arnold & Nelson, U.S. Pat. No. 5,283,174; it will be understood by those of skill in the art that other assay methods employing different detection means, such as radioactive labels, may be used. Each amplification reaction was given 100 μl of a solution of 10 mM lithium succinate (pH 5.0), 2% (w/v) lithium lauryl sulfate, 1 mM mercaptoethanesulfonic acid, 0.3% (w/v) PVP-40, 230 mM LiOH, 1.2M LiCl, 20 mM EGTA, 20 mM EDTA, 100 mM succinic acid (pH 4.7) and 15 mM 2,2'-dipyridyl disulfide containing approximately 75 femtomoles (fmol) of an acridinium ester-labeled oligonucleotide probe ((+) sense) designed to be complementary to the amplified RNA amplicons. Each tube was mixed, incubated at 60° C. for 20 minutes, and then allowed to cool. Each reaction mixture was given 300 μl of a solution containing 0.6M sodium borate (pH 8.5), 1% (v/v) TRITON® X-100 and 182 mM NaOH and incubated for 6 minutes at 60° C. to destroy label unassociated with hybridized probe.

The reaction mixtures were cooled for 5 minutes, and the remaining chemiluminescence was measured in a luminometer (LEADERs Gen-Probe Incorporated, San Diego, Calif.) after an automatic injection of 200 μl 0.1% (v/v) $H_2O_2$, 0.1 mM nitric acid, followed immediately by an injection of 1.0N NaOH. The amount of subsequently emitted light is reported in Relative Light Units (RLU). Under these conditions the background level of light emission was in the range of about 2000 to 4000 RLU.

The results were recorded and tabulated for each temperature of storage (25° C., 35° C. and 45° C.) as indicated below. Each sample was assayed in triplicate and averaged. This average was used to plot the data for each temperature graphically.

TABLE 3

Stability of Lyophilized Enzyme:Amplification Reagent Storage Temperature 25° C.

| Days of Storage | 0 | 11 | 16 | 20 | 30 | 40 | 61 |
|---|---|---|---|---|---|---|---|
| Reagents without DNA Target (RLU) | 2053 | 1911 | 1524 | 2188 | 1851 | 1548 | 1972 |
| | 2130 | 1590 | 1561 | 1990 | 1847 | 1726 | 1655 |
| | 2148 | 1752 | 2037 | 1606 | 1923 | 2382 | 1538 |
| Average RLU | 2110 | 1751 | 1707 | 1928 | 1874 | 1685 | 1722 |
| Reagents with DNA Target (RLU) | 1562029 | 2105440 | 1248988 | 2129935 | 1927067 | 1417883 | 1486111 |
| | 1756224 | 1903081 | 1509929 | 2363198 | 1422699 | 1601071 | 1290950 |
| | 1070164 | 1492458 | 1944566 | 1922529 | 1274124 | 1889588 | 1210344 |
| Average RLU | 1462806 | 1833659 | 1567828 | 2138554 | 1541297 | 1636181 | 1329135 |
| Reagents in Human Serum, No DNA Target (RLU) | 8437 | 2904 | 2660 | 3044 | 2919 | 2465 | 2946 |
| | 3902 | 2893 | 2993 | 3152 | 2971 | 3089 | 3473 |
| | 3534 | 3003 | 2768 | 2951 | 2379 | 2958 | 3686 |
| Average RLU | 5291 | 2933 | 2807 | 3049 | 2756 | 2837 | 3368 |
| Reagents in Human Serum, with DNA Target (RLU) | 1955525 | 2282336 | 2282171 | 1760428 | 2034705 | 1936366 | 1643624 |
| | 2255411 | 2204415 | 1860043 | 1992765 | 2101999 | 1770109 | 1762360 |
| | 2282281 | 2206778 | 1903519 | 2093235 | 2064041 | 1811820 | 1622750 |
| Average RLU | 2164406 | 2231176 | 2015244 | 1948609 | 2066915 | 1839432 | 1676245 |

TABLE 4

Stability of Lyophilized Enzyme:Amplification Reagent Storage Temperature 35° C.

| Days of Storage | 0 | 3 | 9 | 16 | 21 | 50 | 61 |
|---|---|---|---|---|---|---|---|
| Reagents without DNA Target (RLU) | 2429 | 17989 | 1768 | 1878 | 2378 | 1430 | 1559 |
| | 2203 | 1775 | 1649 | 1919 | 2330 | 1411 | 1566 |
| | 1996 | 1891 | 1840 | 2043 | 1995 | 1338 | 1692 |
| Average RLU | 2209 | 7218 | 1752 | 1947 | 2234 | 1393 | 1606 |
| Reagents | 1173260 | 2310573 | 2186899 | 1559681 | 1876363 | 1458120 | 1366068 |

TABLE 4-continued

Stability of Lyophilized Enzyme:Amplification Reagent
Storage Temperature 35° C.

| Days of Storage | 0 | 3 | 9 | 16 | 21 | 50 | 61 |
|---|---|---|---|---|---|---|---|
| with DNA Target (RLU) | 1580018 | 2136598 | 2119044 | 1365165 | 1919833 | 1932847 | 1443874 |
| | 1389614 | 2303010 | 1568334 | 1632416 | 1979406 | 1343433 | 1421081 |
| Average RLU | 1380964 | 2251060 | 1958092 | 1525754 | 1925201 | 1578133 | 1410341 |
| Reagents in Human Serum, No DNA Target (RLU) | 4819 | 3298 | 3608 | 3575 | 2912 | 3074 | 3836 |
| | 4779 | 9577 | 3200 | 3535 | 3422 | 3044 | 4160 |
| | 24541 | 3349 | 3114 | 3712 | 3151 | 3027 | 3901 |
| Average RLU | 11390 | 5408 | 3307 | 3607 | 3162 | 3048 | 3966 |
| Reagents in Human Serum, with DNA Target (RLU) | 1946881 | 2228745 | 2233566 | 2087936 | 1984355 | 2255784 | 1873070 |
| | 2158003 | 2289829 | 2303812 | 2163922 | 2192597 | 2147927 | 1789954 |
| | 2110796 | 2286956 | 2179206 | 2152655 | 2121658 | 2087549 | 2049762 |
| Average RLU | 2071893 | 2268510 | 2238861 | 2134838 | 2099537 | 2163753 | 1904262 |

TABLE 5

Stability of Lyophilized Enzyme/Amplification Reagent
Storage Temperature 45° C.

| Days of Storage | 0 | 6 | 11 | 16 | 33 |
|---|---|---|---|---|---|
| Reagents without DNA Target (RLU) | 2508 | 1613 | 1687 | 2626 | 1594 |
| | 2250 | 1872 | 1781 | 2027 | 1596 |
| | 2159 | 1903 | 2206 | 2056 | 1661 |
| Average RLU | 2306 | 1796 | 1891 | 2236 | 1617 |
| Reagents with DNA Target (RLU) | 1431296 | 1097084 | 975001 | 1320113 | 1017853 |
| | 1329706 | 949892 | 758705 | 939417 | 1368153 |
| | 1288191 | 798877 | 1242188 | 972442 | 1015174 |
| Average RLU | 1349731 | 948618 | 991965 | 1077324 | 1133727 |
| Reagents in Human Serum, No DNA Target (RLU) | 3554 | 3375 | 3011 | 3068 | 3183 |
| | 3109 | 4452 | 3119 | 3559 | 3115 |
| | 4239 | 2960 | 3382 | 3381 | 2826 |
| Average RLU | 3634 | 3596 | 3171 | 3336 | 3041 |
| Reagents in Human Serum, with DNA Target (RLU) | 1663770 | 1850263 | 1691590 | 1691372 | 1615426 |
| | 1677985 | 1868747 | 1684565 | 1709387 | 1913706 |
| | 1747637 | 2016609 | 1646303 | 1765393 | 1799445 |
| Average RLU | 1696464 | 1911873 | 1674153 | 1722051 | 1776192 |

These data show that the co-lyophilized Enzyme:Amplification Reagent prepared in accordance with the method herein described retains all four of the enzymatic activities (RNA-directed DNA polymerase, DNA-directed DNA polymerase, RNAse H, and RNA polymerase) necessary to achieve nucleic acid amplification according to the transcription-mediated amplification method employed. Additionally, the data indicate that there is no noticeable deleterious effect on the nucleotide triphosphates or any other component of the Amplification Reagent when the reagent is co-lyophilized with reverse transcriptase and RNA polymerase.

These results also show that the enzymatic activities of reverse transcriptase and RNA polymerase enzymatic activities are not significantly inhibited when the amplification reaction is performed in the presence of a complex biological sample, such as human serum. Hence, the lyophilized amplification reagent appears to be suitable for use in conjunction with samples such as those obtained in clinical diagnostic settings.

The data can be interpreted in a number of ways; one of the more useful means of interpretation utilizes a form of the Arrhenius equation to predict the stability of the composition over an even greater time than actually tested. The Arrhenius equation is commonly used by those of skill in the art to predict the rates of chemical reactions and the stability of various thermolabile compounds as a function of temperature.

As utilized herein, the Arrhenius equation assumes a first order reaction of enzyme (or reagent) inactivation wherein an active enzyme or reagent has a single rate of inactivation at a given temperature and a single mechanism of inactivation at all tested temperatures. The equation utilized by the Applicant is:

$$ln(k_2/k_1) = (-E_a/R)((T_2-T_1)/(T_2 \times T_1))$$

where $k_2$ equals the rate constant at the experimental temperature (°K), $k_1$ equals the rate constant for the reaction at a reference temperature, $E_a$ equals the activation energy of the reaction, R equals the gas constant (1.987 cal/°K-mole), $T_1$ equals the reference temperature (e.g., 298.16° K (25° C.)), and $T_2$ equals the experimental temperature (expressed in °K).

If $E_a$ is assumed to be 15,000 cal/mole and the reference and experimental temperatures are known, then a ratio of the rate constants $k_2/k_1$ can be determined. In the simple case where both the reference and experimental temperatures are 25° C., the ratio of these constants is 1 since the constants are identical. If the experimental temperature is 35° C. and the reference temperature is 25° C., the predicted ratio will be 2.27. If the experimental temperature is 45° C. and the reference temperature is 25° C., the predicted ratio will be 4.91. Using the same equation, if the reference temperature is 5° C. and the experimental temperature is 45° C., the ratio is 30.33.

The rate constant ratios can be considered the "decomposition ratio" of the experimental storage time to the normal storage time, whether this time is expressed in hours, days, weeks, etc. Therefore, if the lyophilized enzyme/ amplification reagent decomposes to 90% of its original potency in 30 days at 45° C., the Arrhenius equation predicts that it would take 147.3 (30×4.91) days at 25° C. for the activity to be similarly reduced.

Thus, the data demonstrate that the combined components of the lyophilized preparation do not noticeably lose their ability to support amplification in "real time", even after 30 days at 45° C. Moreover, by utilizing the Arrhenius equation the same data predict that the reagents would not suffer a significant loss in activity if the lyophilized reagent was actually stored for almost 5 months at 25° C. or for 2.5 years (30.33×30 days) at 5° C. prior to use.

The Applicant presents these methods of data analysis as an aid to the understanding of the present invention, and does not wish to be limited or bound by theoretical considerations. The actual stability of the compositions of the present invention may vary from the predictions of the Arrhenius equation, which provides general guidance toward predicting the stability of the lyophilized reagents.

Example 4
T7 RNA Polymerase Assay of Lyophilized Reagent

The lyophilized Enzyme:Amplification Reagent prepared in Example 2 was incubated at 35° C. for 0, 3, 9, 16, 21 and 30 days. At each of these time points vials were removed from the stress temperature and stored at −30° C. until the last samples had been collected.

RNA polymerase activity was measured by reconstituting each aliquot of lyophilized reagent in 1.5 ml of Reconstituting Buffer (0.01% (v/v) TRITON® X-100, 41.6 mM $MgCl_2$, 1 mM $ZnC_2H_3O_2$, 10% (v/v) glycerol, 0.3% (v/v) ethanol, 0.02% (w/v) methyl paraben, and 0.01% (w/v) propyl paraben). The reagent was then diluted 100-fold, 200-fold and 400-fold in a solution containing 20 mM HEPES (pH 7.5), 5 mM NALC, 0.1 mM EDTA, 0.1 mM $ZnC_2H_3O_2$, 0.1M NaCl and 0.2% (v/v) TRITON® X-102. A reaction pre-mix was made up separately, containing 22 mM $MgCl_2$, 7.8 mM each of ATP and GTP, 2.5 mM each of CTP and UTP, 62.5 mM Tris (pH 7.5), 2.5 mM spermidine and 0.5 nanomoles of a target nucleic acid. The target was a linearized pUC T7G10 plasmid having a T7 promoter positioned immediately upstream from bacteriophage T7 Gene 10. This plasmid was derived from plasmid pGEMEX-1 (Promega Corporation, Madison, Wis.).

The reaction pre-mix was divided into 40 µl aliquots, and each aliquot was incubated for 3 minutes at 37° C. Ten microliters of each dilution of the Enzyme:Amplification Reagent was added to the warmed pre-mix tubes and incubated for 20 minutes at 37° C. Fifty microliters of a solution of 10 mM lithium succinate, 2% (w/v) lithium lauryl sulfate, 1 mM mercaptoethanesulfonic acid, 0.3% (w/v) PVP-40, 230 mM LiOH, 1.2M LiCl, 20 mM EGTA, 20 mM EDTA, 100 mM succinic acid (pH 4.7) and 15 mM 2.2'-dipyridyl disulfide containing approximately 75 femtomoles of an acridinium ester labeled Gene 10 oligonucleotide probe ((−) sense) designed to be complementary to the transcriptional products was added to each tube. A standard sample containing 10 femtomoles (fmol) of single-stranded DNA complementary to the Gene 10 probe was included in the HPA step to quantitate the amount of RNA produced in the experimental reaction mixtures. Hybridization was performed essentially as in Example 2, except that the hybridization volumes were half as large. Following degradation of the unhybridized label, the remaining acridinium ester was reacted and the emitted light measured in a luminometer as RLU.

The raw data was converted to units of RNA polymerase activity per µl as follows. The raw RLU obtained for the positive control reaction was subtracted from the RLU obtained in the negative control (no target DNA). This figure represents the net amount of emitted light obtained when 10 fmol of RNA are in the sample, and can be expressed as RLU/fmol RNA. Likewise, the RLU obtained for each sample can be subtracted from the background luminescence (RLU per 20 minutes). When this figure is divided by the figure obtained for the standard (RLU per fmol RNA) the result is the number of fmol RNA produced in each reaction per 20 minutes. Because 1 unit RNA polymerase activity was defined as the production of 1 fmol RNA in 20 minutes under the assay conditions, this figure is also the number of units of RNA polymerase activity in each 10 µl volume of enzyme originally added.

The data obtained from these reactions were first plotted for each time of storage at 35° C. by expressing fmol of RNA produced as a function of the number of microliters of the original 1.5 ml reconstituted Enzyme:Amplification Reagent represented in each experimental tube. A simple linear function was described. When the data had been plotted, a best-fit line for the data obtained for each time point was calculated; the slope of this curve was expressed as units of T7 polymerase activity per microliter. When the "zero time" time point is considered as 100% activity, the calculated units of T7 RNA polymerase for each remaining time point was expressed as percent activity remaining.

The results indicate that little if any decrease in T7 RNA polymerase occurs over the 30 day 35° C. incubation period.

Example 5
Reverse Transcriptase Assay of the Lyophilized Reagent

The activity of lyophilized MMLV reverse transcriptase incubated for 3, 9, 16, 21 and 30 days at 35° C. was assayed as follows. Individual vials were removed from the stress temperature at the indicated times and stored at −30° C. until the last samples had been collected.

Each vial was reconstituted in 1.5 ml reconstitution buffer and diluted 100 fold, 200-fold, and 400-fold as in Example 4. A separate reverse transcriptase pre-mix mixture was made containing 5 mM $MgCl_2$, 30 mM KCl, 0.25 mM each of dATP, dTTP, dCTP, and dGTP, 62.5 mM Tris (pH 7.5), 2.5 mM spermidine, 3.75 nM target RNA, and 750 nM of an amplification primer. The target RNA was the T7 Gene 10 RNA transcripts generated in Example 4. The primer was an oligonucleotide 22 bases in length designed to hybridize to a region near the 3' end of the target RNA. Ten microliters of the enzyme dilutions were each added to 40 µl of the reaction pre-mix on ice. The reactions were conducted by incubation at 37° C. for 15 minutes. Each reaction was terminated with the addition of 50 µl of an acridinium ester-labeled hybridization probe. The probe was designed to be complementary to the newly synthesized Gene 10 cDNA.

Detection by HPA was conducted as described in Example 3. Results were measured in RLU.

This assay measured the RNA-directed DNA polymerase activity and the RNAse H activity of the MMLV reverse transcriptase. The latter activity is indirectly measured, since without degradation of the RNA strand of the RNA:DNA hybrid produced by extension of the Gene 10 primer, the probe would not be able to hybridize to the cDNA.

One unit of these combined enzymatic activities was defined as the detection of 1 fmol cDNA in 15 minutes under the reaction conditions described above. Calculation of the units of enzyme activity remaining at each time point and dilution was performed as in Example 4 using 10 fmol of the amplified cDNA as a standard.

The results indicate that little if any decrease in RT activity occurs over the 30 day 35° C. incubation period.

Example 6
Co-Lyophilization of Reverse Transcriptase and RNA Polymerase with Nucleotides and Primers.

The preceding examples have illustrated the preparation and use of a single reagent containing a desiccated preparation of RNA polymerase and reverse transcriptase together with nucleotide triphosphates and co-factors necessary for nucleic acid amplification. It will be clear to one of skill in the art that, given the ability of such a "single vial" reagent to amplify nucleic acids after prolonged storage at raised temperatures, it should easily be possible to include the amplification primer(s) in the lyophilized preparation so as to reduce the number of steps in methods of using such a reagent, and to reduce the number of containers in a kit for nucleic acid amplification from three (for example, lyophilized Enzyme:Amplification Reagent, primers and Reconstitution Reagent) to two (for example, lyophilized Enzyme/primer/Amplification Reagent and Reconstitution Reagent).

Such a preparation is useful when the amplification reaction does not make use of temperatures which will denature one or both of the enzymes, such as when the initial target nucleic acid is RNA and the amplification method is an isothermal one, for example as in Kacian & Fultz, PCT Publication No. WO91/01384 or Kacian et al., PCT Publication No. WO93/22461.

Example 7
Lyophilization of Reverse Transcriptase with Sucrose

Applicant has also discovered that sucrose, (for example, at a concentration of 0.2M), can be used as a cryoprotectant stabilizing agent in the lyophilization of reverse transcriptase; the stabilizing effect of sucrose appears to be good; compared to a standard liquid solution containing MMLV-RT and stored for the same period of time in 50% (v/v) glycerol at $-20°$ C. the preparation lyophilized in 0.2M sucrose maintained 93% of the activity of the standard MMLV-RT preparation following storage of the lyophilizate for 30 days at $4°$ C. A similarly treated lyophilizate containing 0.2M trehalose rather than sucrose showed an average of 105% of the activity of the standard under the same conditions.

Example 8
Lyophilization in the Presence of PVP

Applicant has further discovered that polyvinylpyrrolidone (PVP) improves the stability of a lyophilized T7 RNA polymerase:MMLV-RT:Amplification Reagent preparation when combined with trehalose in a buffer before lyophilization to an even greater degree than when the Enzyme:Amplification Reagent is lyophilized in the presence of trehalose alone. This surprising finding suggests that the stability of the lyophilized Enzyme:Amplification Reagent can be maintained to approximately the same or a greater extent by using PVP alone rather than in a lyophilized composition containing trehalose alone or a combination of trehalose and PVP as a cryoprotectant stabilizing agent. Lyophilization of the enzymes may be optimized by dialyzing the purified enzymes as detailed in Example 2 against Dialysis Solution containing TRITON® X-100 or another non-ionic solubilizing agent. The Dialysis Solution does not contain trehalose. Following the buffer exchange step, aliquots of the enzyme solution can be made and various amounts of PVP added to each aliquot. The aliquots can then be given the Enzyme:Amplification Reagent and lyophilized as detailed in Example 2. These lyophilized samples may be incubated at different temperatures for various times and assayed for each enzymatic activity and for the reconstituted reagent's ability to support nucleic acid amplification as in Example 3.

It will be understood by those of skill in the art that the above examples only describe preferred embodiments of the methods and compositions of the present invention, and are not intended to limit or define the invention. Other embodiments are contained in the claims which follow these examples.

What is claimed is:

1. A composition for amplification of a target nucleic acid comprising a single lyophilizate comprising:
   a) an effective amount of an RNA-directed DNA-polymerase activity, a DNA-directed DNA-polymerase activity, an RNAse H activity, and a DNA-directed RNA polymerase activity wherein the RNA-directed DNA polymerase activity, the DNA-directed DNA-polymerase activity, and the RNAse H activity are provided by at least one enzyme;
   b) one or more stabilizing agents having cryoprotectant activity selected from the group consisting of a non-reducing disaccharide and polyvinylpyrrolidone;
   c) deoxyribonucleotide triphosphates and ribonucleotide triphosphates,
wherein when said lyophilizate is reconstituted by addition of an aqueous solvent, the resulting solution will amplify a single-stranded RNA molecule having a target nucleotide sequence region when contacted with one or more suitable oligonucleotide primers under appropriate nucleic acid amplification conditions.

2. The composition of claim 1 wherein said lyophilizate further comprises said one or more suitable primers.

3. The composition of claim 1 wherein said RNA-directed DNA polymerase activity, said DNA-directed DNA polymerase activity, and said RNAse H activity are provided by a recombinant retroviral reverse transcriptase, and said DNA-directed RNA polymerase activity is provided by a bacteriophage RNA polymerase.

4. The composition of claim 3 wherein said reverse transcriptase is derived from Moloney murine leukemia virus.

5. The composition of claim 3 wherein said RNA polymerase is derived from T7 bacteriophage.

6. The composition of claim 1 wherein said stabilizing agent is a mixture of a non-reducing disaccharide and polyvinylpyrrolidone.

7. The composition of claim 1 wherein said stabilizing agent is selected from the group consisting of sucrose, trehalose, and polyvinylpyrrolidone.

8. The composition of claim 1 wherein said stabilizing agent comprises trehalose.

9. A composition for amplification of a target nucleic acid comprising a single lyophilizate comprising:
   a) an effective amount of an RNA-directed DNA polymerase activity, a DNA-directed DNA polymerase activity, an RNAse H activity, and a DNA-directed RNA polymerase activity wherein the RNA-directed DNA polymerase activity, the DNA-directed DNA polymerase activity, and the RNAse H activity are provided by at least one enzyme;
   b) one or more stabilizing agents having cryoprotectant activity selected from the group consisting of a non-reducing disaccharide and polyvinylpyrrolidone; and
   c) deoxyribonucleotide triphosphates and ribonucleotide triphosphates,
but provided said composition does not contain a carboxylic acid, wherein when said lyophilizate is reconstituted by addition of an aqueous solvent the resulting solution will amplify a single-stranded RNA molecule having a target nucleotide sequence region when contacted with one or more suitable oligonucleotide primers under appropriate nucleic acid amplification conditions.

10. The composition of claim 9 wherein said RNA-directed DNA polymerase activity, said DNA-directed DNA polymerase activity, and said RNAse H activity are provided by a recombinant retroviral reverse transcriptase, and said DNA-directed RNA polymerase activity is provided by a bacteriophage RNA polymerase.

11. The composition of claim 10 wherein said reverse transcriptase is derived from Moloney murine leukemia virus.

12. The composition of claim 10 wherein said RNA polymerase is derived from T7 bacteriophage.

13. The composition of claim 9 wherein said stabilizing agent comprises a mixture of a non-reducing disaccharide and polyvinylpyrrolidone.

14. The composition of claim 9 wherein said stabilizing agent comprises trehalose.

15. The composition of claim 9 wherein said stabilizing agent comprises polyvinylpyrrolidone.

16. The composition of claim 15 wherein said stabilizing agent further comprises trehalose.

17. A composition comprising reverse transcriptase lyophilized in the presence of at least one member of the group consisting of sucrose, trehalose, or polyvinylpyrrolidone, wherein, upon reconstitution, said lyophilized enzyme is able to support nucleic acid amplification in a reaction mixture containing an RNA polymerase.

18. A composition comprising RNA polymerase lyophilized in the presence of at least one member of the group consisting of sucrose, trehalose, or polyvinylpyrrolidone, wherein, upon reconstitution, said lyophilized enzyme is able to support nucleic acid amplification in a reaction mixture containing reverse transcriptase.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

AATTAATAC GACTCACTAT AGGGAGAGAG AAGTGGTCAC GGAGGTAC    4 8

( 2 ) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CATGACTGGT GGACAGCAAA TG                                                                                          22

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CTGCTGGAGA TAAACTGGCG TTGTTC                                                                                      26